United States Patent
Anderson et al.

(10) Patent No.: US 7,029,451 B2
(45) Date of Patent: Apr. 18, 2006

(54) EXCISIONAL DEVICES HAVING SELECTIVE CUTTING AND ATRAUMATIC CONFIGURATIONS AND METHODS OF USING SAME

(75) Inventors: Scott C. Anderson, Sunnyvale, CA (US); Daniel M. Brounstein, Fremont, CA (US); Ary S. Chernomorsky, Walnut Creek, CA (US); Mark J. Clifford, Los Altos, CA (US); James W. Vetter, Portola Valley, CA (US)

(73) Assignee: Rubicor Medical, Inc., Redwood City, CA (US)

( * ) Notice: Subject to any disclaimer, the term of this patent is extended or adjusted under 35 U.S.C. 154(b) by 222 days.

(21) Appl. No.: 10/290,051

(22) Filed: Nov. 6, 2002

(65) Prior Publication Data

US 2004/0087872 A1     May 6, 2004

(51) Int. Cl.
*A61B 10/00*     (2006.01)
(52) U.S. Cl. .................................................. 600/564
(58) Field of Classification Search ............... 600/562, 600/564, 566, 567; 606/170, 46, 47, 79, 606/80
See application file for complete search history.

(56) References Cited

U.S. PATENT DOCUMENTS

| | | |
|---|---|---|
| 1,813,902 A | 7/1931 | Bovie |
| 2,816,552 A | 12/1957 | Hoffman |
| 3,320,957 A | 5/1967 | Sokolik |
| 3,732,858 A | 5/1973 | Banko |
| 3,749,085 A | 7/1973 | Willson |
| 3,910,279 A | 10/1975 | Okada et al. |
| 3,955,578 A | 5/1976 | Chamness et al. |
| 4,099,518 A | 7/1978 | Baylis et al. |
| 4,245,653 A | 1/1981 | Weaver |
| 4,347,846 A | 9/1982 | Dormia |
| 4,611,594 A | 9/1986 | Grayhack |
| 4,650,466 A | 3/1987 | Luther |
| 4,890,611 A | 1/1990 | Monfort |
| 4,903,696 A | 2/1990 | Stasz et al. |
| 4,966,604 A | 10/1990 | Reiss |
| 5,071,424 A | 12/1991 | Reger |
| 5,083,570 A | 1/1992 | Mosby |
| 5,100,423 A | 3/1992 | Fearnot |
| 5,147,355 A | 9/1992 | Friedman et al. |
| 5,152,293 A | 10/1992 | Vonesh et al. |
| 5,156,610 A | 10/1992 | Reger |
| 5,174,296 A | 12/1992 | Watanabe et al. |
| 5,176,688 A | 1/1993 | Narayan |
| 5,192,291 A | 3/1993 | Pannek |
| 5,211,651 A | 5/1993 | Reger |
| 5,217,479 A | 6/1993 | Shuler |
| 5,224,488 A | 7/1993 | Neuffer |
| 5,224,945 A | 7/1993 | Pannek et al. |
| 5,282,484 A | 2/1994 | Reger |
| 5,308,321 A | 5/1994 | Castro |

(Continued)

FOREIGN PATENT DOCUMENTS

DE     195 28 440 A1     2/1997

(Continued)

*Primary Examiner*—Max F. Hindenburg
*Assistant Examiner*—Brian Szmal
(74) *Attorney, Agent, or Firm*—Young Law Firm, P.C.

(57) ABSTRACT

Surgical devices include a selectively cutting and atraumatic distal tip that is configured to assume a first configuration in which cutting surface or surfaces thereof are effective to cut tissue and a second configuration in which the cutting surface or surfaces thereof are ineffective to cut tissue.

50 Claims, 9 Drawing Sheets

U.S. PATENT DOCUMENTS

| | | |
|---|---|---|
| 5,318,576 A | 6/1994 | Plassche |
| 5,325,860 A | 7/1994 | Seward et al. |
| 5,415,656 A | 5/1995 | Tihon et al. |
| 5,441,510 A | 8/1995 | Simpson et al. |
| 5,527,326 A | 6/1996 | Hermann |
| 5,554,163 A | 9/1996 | Shturman |
| 5,630,426 A | 5/1997 | Eggers et al. |
| 5,632,754 A | 5/1997 | Farley et al. |
| 5,672,172 A | 9/1997 | Zupkas |
| 5,709,697 A | 1/1998 | Ratcliff |
| 5,766,191 A | 6/1998 | Trerotola |
| 5,794,626 A | 8/1998 | Kieturakis |
| 5,895,399 A | 4/1999 | Barbut et al. |
| 5,913,855 A | 6/1999 | Gough et al. |
| 5,928,159 A | 7/1999 | Eggers et al. |
| 5,928,164 A | 7/1999 | Burbank |
| 5,947,964 A | 9/1999 | Eggers et al. |
| 5,954,655 A | 9/1999 | Hussman |
| 5,954,670 A | 9/1999 | Baker |
| 6,015,390 A | 1/2000 | Krag |
| 6,022,362 A | 2/2000 | Lee |
| 6,036,708 A | 3/2000 | Sciver |
| 6,063,082 A | 5/2000 | DeVore |
| 6,080,149 A | 6/2000 | Huang |
| 6,080,151 A | 6/2000 | Swartz et al. |
| 6,096,053 A | 8/2000 | Bates |
| 6,099,534 A | 8/2000 | Bates |
| 6,106,524 A | 8/2000 | Eggers et al. |
| 6,179,860 B1 | 1/2001 | Fulton, III et al. |
| 6,221,006 B1 | 4/2001 | Dubrul et al. |
| 6,238,389 B1 | 5/2001 | Paddock et al. |
| 6,280,450 B1 | 8/2001 | McGuckin, Jr. |
| 6,325,797 B1 | 12/2001 | Stewart et al. |
| 6,331,166 B1 | 12/2001 | Burbank |
| 6,387,056 B1 | 5/2002 | Kieturakis |
| 6,514,248 B1 | 2/2003 | Eggers et al. |
| 6,589,240 B1 * | 7/2003 | Hinchliffe .................... 606/47 |
| 6,602,204 B1 | 8/2003 | Dubrul et al. |
| 6,605,047 B1 | 8/2003 | Zarins et al. |
| 2001/0047169 A1 | 11/2001 | McGuckin, Jr. |
| 2002/0058885 A1 | 5/2002 | Burbank et al. |
| 2002/0077648 A1 * | 6/2002 | Lee et al. .................... 606/170 |
| 2002/0183758 A1 * | 12/2002 | Middleton et al. ............ 606/79 |

FOREIGN PATENT DOCUMENTS

| | | |
|---|---|---|
| DE | 197 06 751 A1 | 2/1997 |
| EP | 0 472 368 B1 | 2/1992 |
| EP | 0 829 232 A2 | 3/1998 |
| EP | 0 829 232 A3 | 3/1998 |
| EP | 0 908 156 B1 | 11/2003 |
| FR | 2 275 226 | 5/1975 |
| GB | 1 331 468 | 9/1973 |
| GB | 2 204 496 A | 11/1988 |
| GB | 2 311 468 A | 1/1997 |
| NL | 1.004723 | 9/1912 |
| SU | 1235497 A1 | 6/1986 |
| SU | 1355266 A1 | 11/1987 |
| WO | WO 92/20291 | 11/1992 |
| WO | WO 95/02370 | 1/1995 |
| WO | WO 95/02371 | 1/1995 |
| WO | WO 96/29946 | 10/1996 |
| WO | WO 98/08441 | 3/1998 |
| WO | WO 99/01074 | 1/1999 |
| WO | WO 99/04704 | 2/1999 |
| WO | WO 99/43262 | 9/1999 |
| WO | WO 99/44506 | 10/1999 |
| WO | WO 99/53851 | 10/1999 |
| WO | WO 00/10471 | 3/2000 |
| WO | WO 00/12009 | 3/2000 |
| WO | WO 00/16697 | 3/2000 |
| WO | WO 00/30531 | 6/2000 |
| WO | WO 00/33743 | 6/2000 |
| WO | WO 00/44295 | 8/2000 |
| WO | WO 00/45854 | 8/2000 |
| WO | WO 00/74561 A1 | 12/2000 |
| WO | WO 01/28445 A1 | 4/2001 |
| WO | WO 01/28446 A1 | 4/2001 |

* cited by examiner

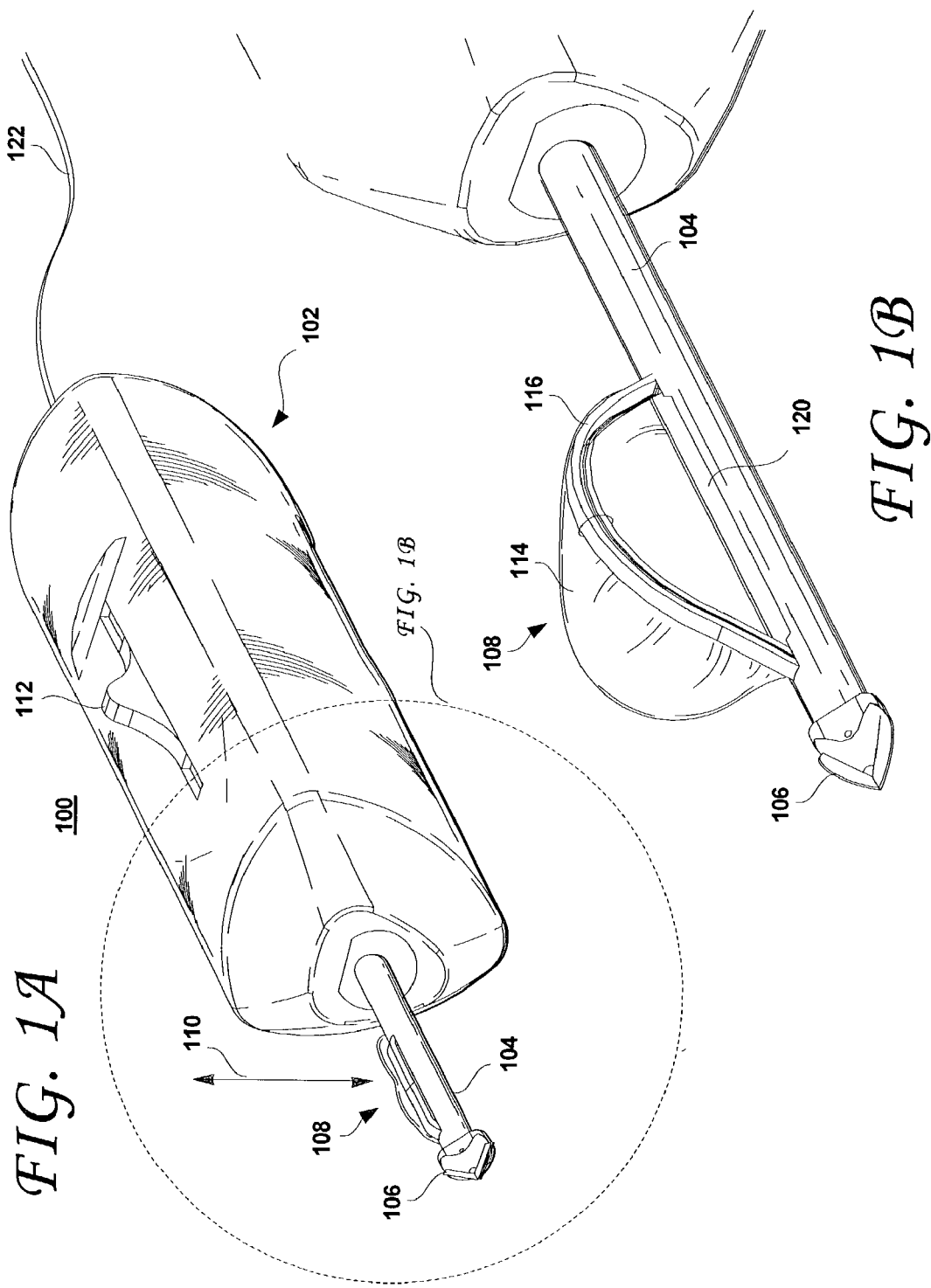

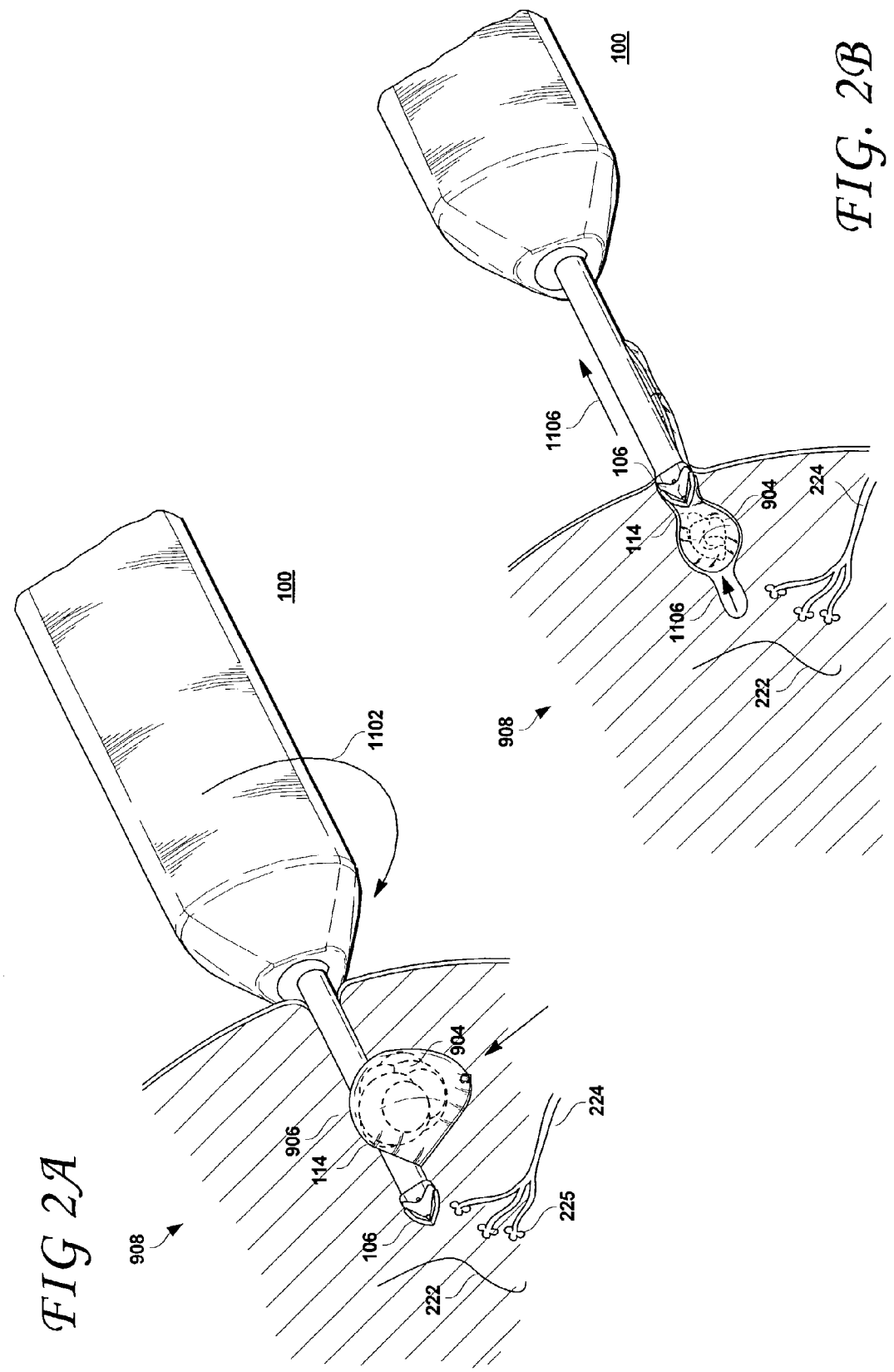

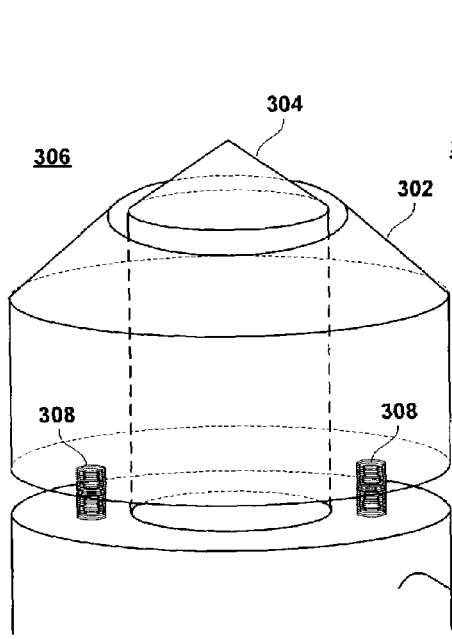
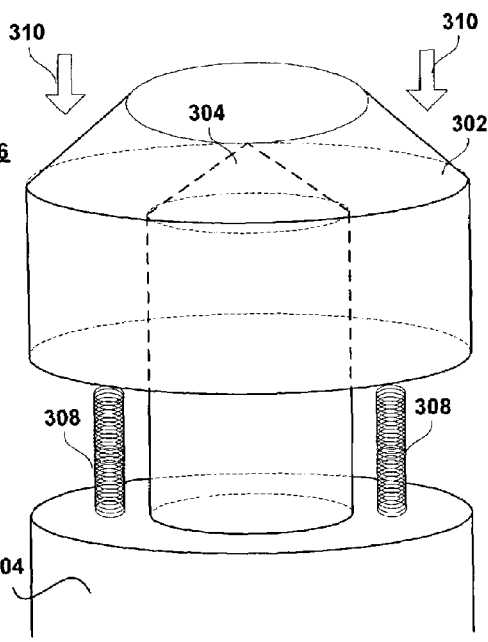
FIG. 3A    FIG. 3B
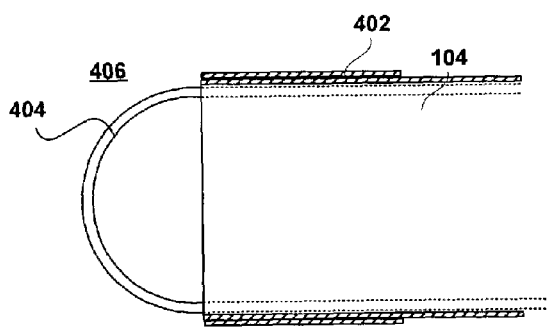
FIG. 4A
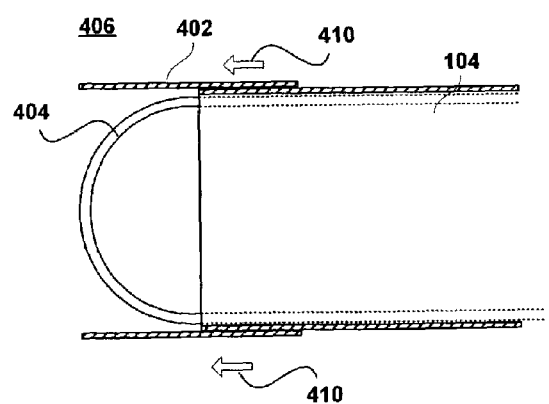
FIG. 4B

EXCISIONAL DEVICES HAVING SELECTIVE CUTTING AND ATRAUMATIC CONFIGURATIONS AND METHODS OF USING SAME

BACKGROUND OF THE INVENTION

1. Field of the Invention

The present invention pertains to the field of surgical devices. In particular, the present invention relates to distal tips for such devices and associated methods for treating soft tissue, such as breast tissue.

2. Description of the Related Art

Breast cancer is a major threat and concern to women. Early detection and treatment of suspicious or cancerous lesions in the breast has been shown to improve long-term survival of the patient. The trend is, therefore, to encourage women not only to perform monthly self-breast examination and obtain a yearly breast examination by a qualified physician, but also to undergo annual screening mammography commencing at age 40. Mammography is the only screening modality available today that can detect small, nonpalpable lesions. These nonpalpable lesions may appear as opaque densities relative to normal breast parenchyma and fat or as clusters of microcalcifications.

The conventional method for diagnosing, localizing and excising nonpalpable lesions detected by mammography generally involves a time-consuming, multi-step process. First, the patient goes to the radiology department where the radiologist finds and localizes the lesion either using mammography or ultrasound guidance. Once localized, a radio-opaque wire is inserted into the breast. The distal end of the wire may include a small hook or loop. Ideally, this is placed adjacent to the suspicious area to be biopsied. The patient is then transported to the operating room. Under general or local anesthesia, the surgeon performs a procedure called a needle-localized breast biopsy. In the needle-localized breast biopsy, the surgeon, guided by the wire previously placed in the patient's breast, excises a mass of tissue around the distal end of the wire. The specimen is sent to the radiology department where a specimen radiograph is taken to confirm that the suspicious lesion is contained within the excised specimen. Meanwhile, the surgeon, patient, anesthesiologist and operating room staff, wait in the operating room for confirmation of that fact from the radiologist before the operation is completed. The suspicious lesion should ideally be excised in toto with a small margin or rim of normal breast tissue on all sides. Obtaining good margins of normal tissue is extremely dependent upon the skill and experience of the surgeon, and often an excessively large amount of normal breast tissue is removed to ensure that the lesion is located within the specimen. This increases the risk of post-operative complications, including bleeding and permanent breast deformity. As 80% of breast biopsies today are benign, many women unnecessarily suffer from permanent scarring and deformity from such benign breast biopsies.

More recently, less invasive techniques have been developed to sample or biopsy the suspicious lesions to obtain a histological diagnosis. The simplest of the newer techniques is to attempt visualization of the lesion by external ultrasound. If seen by external ultrasound, the lesion can be biopsied while being continuously visualized. This technique allows the physician to see the biopsy needle as it actually enters the lesion, thus ensuring that the correct area is sampled. Current sampling systems for use with external ultrasound guidance include a fine needle aspirate, core needle biopsy or vacuum-assisted biopsy devices.

Another conventional technique localizes the suspicious lesion using stereotactic digital mammography. The patient is placed prone on a special table that includes a hole to allow the designated breast to dangle therethrough. The breast is compressed between two mammography plates, which stabilizes the breast to be biopsied and allows the digital mammograms to be taken. At least two images are taken 30 degrees apart to obtain stereotactic views. The x, y and z coordinates targeting the lesion are calculated by a computer. The physician then aligns a special mechanical stage mounted under the table that places the biopsy device into the breast to obtain the sample or samples. There are believed to be three methods available to biopsy lesions using a stereotactic table: (1) fine needle aspiration, (2) core needle biopsy and (3) vacuum-assisted core needle biopsy.

Fine needle aspiration uses a small gauge needle, usually 20 to 25 gauge, to aspirate a small sample of cells from the lesion or suspicious area. The sample is smeared onto slides that are stained and examined by a cytopathologist. In this technique, individual cells in the smears are examined, and tissue architecture or histology is generally not preserved. Fine needle aspiration is also very dependent upon the skill and experience of the operator and can result in a high non-diagnostic rate (up to about 83%), due to inadequate sample collection or preparation.

Core needle biopsy uses a larger size needle, usually 14 gauge to sample the lesion. Tissue architecture and histology are preserved with this method. A side-cutting device, consisting of an inner trough with an outer cutting cannula is attached to a spring-loaded device for a rapid semi-automated firing action. After the lesion is localized, local anaesthetic is instilled and a small incision is made in the skin with a scalpel. The device enters the breast and the needle tip is guided into the breast up to the targeted lesion. The device is fired. First, the inner cannula containing the trough rapidly penetrates the lesion. Immediately following this, the outer cutting cannula rapidly advances over the inner cannula cutting a sample of tissue off in the trough. The whole device is then removed and the sample retrieved. Multiple penetrations of the core needle through the breast and into the lesion are required to obtain an adequate sampling of the lesion. Over 10 samples have been recommended by some.

The vacuum-assisted breast biopsy system is a larger semi-automated side-cutting device. It is usually 11 gauge in diameter and is more sophisticated than the core needle biopsy device. Multiple large samples can be obtained from the lesion without having to reinsert the needle each time. A vacuum is added to suck the tissue into the trough. The rapid firing action of the spring-loaded core needle device is replaced with an oscillating outer cannula that cuts the breast tissue off in the trough. The physician controls the speed at which the outer cannula advances over the trough and can rotate the alignment of the trough in a clockwise fashion to obtain multiple samples.

If a fine needle aspirate, needle core biopsy or vacuum-assisted biopsy shows malignancy or a specific benign diagnosis of a typical hyperplasia, then the patient needs to undergo another procedure, the traditional needle-localized breast biopsy, to fully excise the area with an adequate margin of normal breast tissue. Sometimes the vacuum-assisted device removes the whole targeted lesion. If this occurs, a small titanium clip should be placed in the biopsy field. This clip marks the area if a needle-localized breast biopsy is subsequently required for the previously mentioned reasons.

Another method of biopsying the suspicious lesion utilizes a large end-cutting core device measuring 0.5 cm to 2.0 cm in diameter. This also uses the stereotactic table for stabilization and localization. After the lesion coordinates are calculated and local anesthesia instilled, an incision large enough to permit entry of the bore is made at the entry site with a scalpel. The breast tissue is cored down to and past the lesion. Once the specimen is retrieved, the patient is turned onto her back and the surgeon cauterizes bleeding vessels under direct vision. The incision, measuring 0.5 to larger than 2.0 cm is sutured closed.

The stereotactic table requires awkward positioning of the patient and may be extremely uncomfortable. The woman must lie prone during the entire procedure, which may be impossible for some patients. In addition, the lesion to be biopsied must be in the center working area of the mammography plates. This may be extremely difficult and uncomfortable for the patient if the lesion is very posterior near the chest wall or high towards the axilla.

The woman is subjected to increased radiation exposure as multiple radiographs are required throughout the course of the procedure to: (1) confirm that the lesion is within the working area of the mammography plates, (2) obtain the stereotactic coordinates (at least two views), (3) verify the positioning of the biopsy needle prior to obtaining tissue, and (4) verify that the lesion was indeed sampled. If any difficulty is encountered during the procedure, additional radiographic exposures are required to verify correction of the problem.

Using the core needle biopsy or vacuum-assisted device, bleeding is controlled only by manual pressure. Bleeding is generally not an issue with fine needle aspiration, but is a legitimate complication of the former two methods. Ecchymoses, breast edema and hematomas can occur. This causes increased post-procedural pain and delays healing. Rarely, the patient may require an emergency operation to control and evacuate a tense hematoma.

Another major concern is the possibility of tumor dissemination. The core needle biopsy and vacuum-assisted devices both cut into the tumor and carve out multiple samples for examination. While cutting into the tumor, cancerous cells may be dislodged cutting across blood vessels at the same time may allow the freed cancerous cells access to the blood stream, thus possibly seeding the tumor beyond its original locus. The long-term consequences of tumor seeding with the risk of bloodborne metastases are unknown at this time, as the techniques are relatively new. However, documented instances of cancerous cells seeding locally into needle tracks exist. There are numerous reports of metastases growing in needle tracks from previous biopsies of a cancerous mass. Most of these are from lung or liver cancers. However, at least one case of mucinous carcinoma of the breast growing in a needle track has been reported. The long-term consequences of neoplasm seeding into needle tracks are currently unknown, again because the techniques are relatively new. Some recommend excision of the entire needle track, including the skin entry site, during the definitive surgical procedure for a diagnosed cancer, whether it is a lumpectomy or a mastectomy. Others assume that with a lumpectomy, the post-operative radiation therapy will destroy any displaced cancer cells in the needle track. With the trend towards treating very small cancers only by excision and without a post-excision course of radiation therapy, the risk of cancer cells metastasizing and growing in needle tracks is very real.

The large core cutting device (0.5 cm to 2.0 cm) generally eliminates the risk of needle track seeding as it is designed to excise the lesion intact. A stereotactic table is required with the same inherent awkwardness for the patient, as discussed above. Bleeding is controlled, albeit manually, requiring that the patient wait until the end of the procedure to be turned over. Compression is used to stabilize the breast and localize the lesions. The breast, however, may be torqued and distorted between the compression plates such that when the plates are removed after the biopsy, the large core track left behind may not be straight, but actually tortuous. This can result in permanent breast deformity.

The location of the insertion site into the breast is dictated by the positioning of the breast in the machine and not by the physician. The entry site is usually away from the nipple-areolar complex and is usually located on the more exposed areas of the breast. For the fine needle aspirate, core biopsy and vacuum-assisted devices, the incision is usually very small and the scar almost unappreciable. However, in the case of the large core biopsy device (0.5 to 2.0 cm), a large incision is needed. Such a large incision often results in a non-aesthetically placed scar.

The newer conventional minimally invasive breast biopsy devices have improved in some ways the ability to diagnose mammographically detected nonpalpable lesions. These devices give the patient a choice as to how she wants the diagnosis to be made. Moreover, these devices are substantially less expensive than the older traditional needle-localized breast biopsy. They are not, however, the final solution. Due to the above-discussed problems and risks associated with compression, needle-track seeding, blood borne metastases, bleeding, radiation exposure and awkwardness of the stereotactic table, more refined devices and methods are needed to resolve these issues. Also, the conventional biopsy devices do not consider margins in their excisions and if cancer is diagnosed, the patient must undergo a needle-localized breast lumpectomy to ensure that adequate margins are removed around the cancer. Devices and methods, therefore, must address the problem of obtaining adequate margins so that a second procedure is not required. Many excisional devices include a fixed distal tip that cuts through the tissue as the device is advanced through the tissue. Such distal tips may be RF energized or simply include a sharp tissue-cutting surface. Current trends in such excisional devices appear to favor devices that include assemblies to cut and isolate the cut specimen from the surrounding tissue prior to retraction of the device from the tissue, to minimize the possibility of seeding the retraction path of the device with potentially cancerous cells. However, while retracting a cut and isolated specimen from the surrounding mass of tissue, the cutting edge of the distal tip may damage the cutting and/or isolating assemblies, especially if the cut and isolated specimen trails the distal tip of the device as the device is retracted from the tissue.

Moreover, the distal cutting tip of known current excisional devices may prevent the excisional device from operating in close proximity to structures in the body that must not be damaged or cut by the excisional device. Indeed, the length of the distal cutting tip of conventional excisional devices may prevent the device from cutting and collecting suspicious lesions that are located immediately adjacent to such structures, such as organs, blood vessels or the like. What are needed, therefore, are surgical devices that address such problems. What are also needed are methods of retrieving tissue specimen that enable physicians to excise, collect and isolate tissue specimen that are located adjacent to such sensitive structures without damage.

SUMMARY OF THE INVENTION

The present invention may be viewed as a method of retrieving a specimen from a mass of tissue, including providing a device having a proximal and a distal end and including, near the distal end, a tissue cutter adapted to cut the specimen from the mass of tissue and a specimen collector adapted to collect the cut specimen, the device further including a tip disposed at the distal end thereof, the tip being configured to selectably assume a first configuration that is effective to cut tissue and a second configuration that is ineffective to cut tissue-causing the tip to assume the first configuration; inserting the device into the mass of tissue with the tip in the first configuration; causing the tip to assume the second configuration; moving the tissue cutter to cut the specimen from the mass of tissue; moving the tissue collector to collect the cut specimen, and retracting the device from the mass of tissue while the tip remains in the second configuration.

A step may be carried out of advancing the device within the mass of tissue over a distance substantially equal to a length of the tip after the causing step. The tip may be biased to assume the second configuration and the inserting step may cause the tip to assume the first configuration. Tip may be spring-mounted and the second causing step may be carried out by stopping the forward movement imposed upon the device in the inserting step. The tissue collector moving step may draw a thin flexible sheath over the cut specimen. The tissue collector moving step may include collecting the specimen and isolating the collected specimen from contact with the surrounding tissue. The tip may include a cutting surface that extends away from the distal tip of the device in the first configuration and the second causing step may include at least partially retracting the cutting surface within the tip. The tip may include a cutting surface or edge that is exposed to the mass of tissue in the first configuration and not exposed to the mass of tissue in the second configuration. The tip may include a cutting surface that is uncovered and exposed to the mass of tissue in the first configuration and the second causing step may include covering the cutting surface such that the cutting surface is not exposed to the mass of tissue. The tissue cutter and the tissue collector may be integrated and the moving steps may be carried out simultaneously. The first and second causing steps may include steps of inflating and deflating a bladder, respectively. The first and second causing steps may include steps of deflating and inflating a bladder, respectively.

The present invention is also a method of retrieving a specimen from a mass of tissue, comprising advancing an excisional device through the mass of tissue and creating a dissection path, the device including a radially extendible tissue cut and collect assembly and a selectively atraumatic and cutting distal tip, the tip being in a first configuration that is effective to cut tissue; causing the tip to assume a second configuration that is ineffective to cut tissue; operating the cut and collect assembly to cut and collect the specimen from the mass of tissue; removing the excisional device and the collected specimen from the mass of tissue with the tip in the second configuration.

A step of further advancing the excisional device along the dissection path after the tip assumes the second configuration may also be carried out. The further advancing step may advance the excisional device along the dissection path a distance that is less than or equal to a length of the tip that is exposed to the mass of tissue when the tip is in the first configuration.

The present invention, according to another embodiment thereof, is a device to cut and collect a specimen from a mass of tissue, comprising: a shaft defining a proximal and a distal end; a cut and collect assembly on the shaft near the distal end, the cut and collect assembly being configured to cut the specimen from the mass of tissue and to collect the cut specimen; and a selectively atraumatic and cutting tip disposed at the distal end of the shaft, the tip including a tissue cutting surface or edge that is configured to selectably assume a first configuration that is effective to cut tissue and a second configuration that is ineffective to cut tissue.

The cutting surface may extend beyond the distal end of the shaft when the tip is in the first configuration and the cutting surface may be at least partially retracted within the shaft when the tip is in the second configuration. The cutting surface may extend beyond the distal end of the shaft when the tip is in the first configuration and wherein the cutting surface is at least partially covered when the tip is in the second configuration. The tip may be configured to pivot between the first and second configurations. The tip may include a resilient member that exerts a biasing force that biases the cutting surface to assume the second configuration. The tip may be configured such that when the device is advanced into the mass of tissue, a force exerted by the mass of tissue against the tip overcomes the biasing force and causes the tip to assume the first configuration. The tip may further include a selectively inflatable bladder that is configured to cause the cutting surface to assume the first configuration when inflated and the second configuration when deflated. The tip may further include a selectively inflatable bladder that is configured to cause the cutting surface to assume the first configuration when deflated and the second configuration when inflated. The tissue cutting surface may be resiliently deformable and may be configured to extend away from the shaft in the first configuration and may be configured to retract within the shaft in the second configuration. The tip may include a guard that is configured to slide on the shaft to selectively expose and cover the tissue cutting surface. The tissue cutting surface may be a distal extension of the cut and collect assembly. The tissue cutting surface may be configured to assume the second configuration when the cut and collect assembly is operative to cut and collect tissue.

The present invention, according to another embodiment thereof, is a surgical device for acting upon biological tissue, comprising a shaft defining a proximal end and a distal end; a work assembly adapted to act upon the tissue, the work assembly being disposed near the distal end of the shaft and including a sheath that may be configured to at least partially trail the distal end of the shaft as the device may be removed from the tissue, and a distal tip, the distal tip including a cutting surface that may be adapted to cut the tissue, the distal tip being configured such that the cutting surface does not damage the sheath as the device is removed from the tissue.

The cutting surface may be energizable by an RF energy source. Alternatively, the cutting surface may be sufficiently sharp to dissect the tissue when the device is inserted into the tissue. The sheath may include a thin flexible membrane and may be attached to the tissue cutter. The work assembly may include a tissue cutter and the sheath may be configured to collect the tissue cut by the tissue cutter. The sheath may be configured to isolate the cut tissue from surrounding tissue.

The cutting surface may be formed of a shape memory material. The cutting surface may be configured to assume a first configuration that is effective to cut tissue when subjected to a first temperature range and to assume a second configuration that is ineffective to cut tissue when subjected to a second temperature range. The distal tip may include a selectively inflatable bladder that is configured to selectively cover and uncover the cutting surface. The distal tip may include a selectively inflatable bladder configured to expose the cutting surface to surrounding tissue when inflated and to move the cutting surface away from the surrounding tissue when deflated. The cutting surface may be coupled to the work element such that when the work element is in an inoperative configuration, the cutting surface is effective to cut tissue and when the work element is in an operative position, the cutting surface is ineffective to cut tissue. The cutting may be configured to pivot between a first configuration in which it is effective to cut tissue and a second configuration in which it is ineffective to cut tissue.

The present invention is also a surgical device, comprising a shaft defining a proximal and a distal end, an actuator attached near the proximal end of the shaft, a work element configured to act upon tissue, the work element being coupled to the actuator and disposed near the distal end of the shaft and a distal tip fitted to the distal end of the shaft, the distal tip being configured to assume a first configuration in which the distal tip extends a first distance from the distal end of the shaft and is effective to cut tissue and a second configuration in which the distal tip extends a second distance from the distal end of the shaft and is ineffective to cut tissue, the second distance being less than the first distance.

The distal tip may be coupled to the actuator. Alternatively, the distal tip may be configured to be operated independently of the work element. The distal tip may include an inflatable bladder and the bladder may be inflated when the distal tip is in the first configuration and at least partially deflated when the distal tip is in the second configuration. The distal tip may include a resiliently deformable cutting surface that is adapted to cut tissue. The distal tip may be coupled to the work element such that when the work element is in an inoperative configuration, the distal tip is in the first configuration and when the work element is in an operative position, the distal tip is in the second configuration. The distal tip may be configured to assume the first configuration when subjected to a temperature that is above a predetermined threshold temperature and to assume the second configuration when subjected to a temperature that is below the predetermined threshold temperature. The distal tip may be biased to assume the second configuration. The distal tip 110 may be coupled to a resilient member that imposes a biasing force on the distal tip, the biasing force causing the distal tip to assume the second configuration until a mechanical force is imposed upon the distal tip that overcomes the biasing force.

BRIEF DESCRIPTION OF THE DRAWINGS

For a further understanding of the objects and advantages of the present invention, reference should be made to the following detailed description, taken in conjunction with the accompanying figures, in which:

FIG. 1A shows an excisional biopsy device having a distal tip.

FIG. 1B is a detail of the excisional biopsy device of FIG. 1A.

FIG. 2A shows the excisional device of FIGS. 1A and 1B in use, cutting and collecting a specimen of soft tissue.

FIG. 2B shows the excisional device of FIG. 2A while being retracted from the patient, illustrating the potential for damage to the sheath of the collection assembly.

FIG. 3A shows a selectively atraumatic and cutting tip according to an embodiment of the present invention, wherein the cutting surface of the cutting tip is in a first configuration that is effective to cut tissue.

FIG. 3B shows the cutting tip of FIG. 3A, in which the cutting surface of the cutting tip is in a second configuration that is ineffective to cut tissue.

FIG. 4A is a modified cross-section of a selectively atraumatic and cutting distal tip according to yet another embodiment of the present invention, in which the cutting surface thereof is in a first configuration that is effective to cut tissue.

FIG. 4B shows the distal cutting tip of FIG. 4A, wherein the cutting surface thereof is in a second configuration that is ineffective to cut tissue.

DESCRIPTION OF THE PREFERRED EMBODIMENTS

Figures 5A, 5B, 5C:
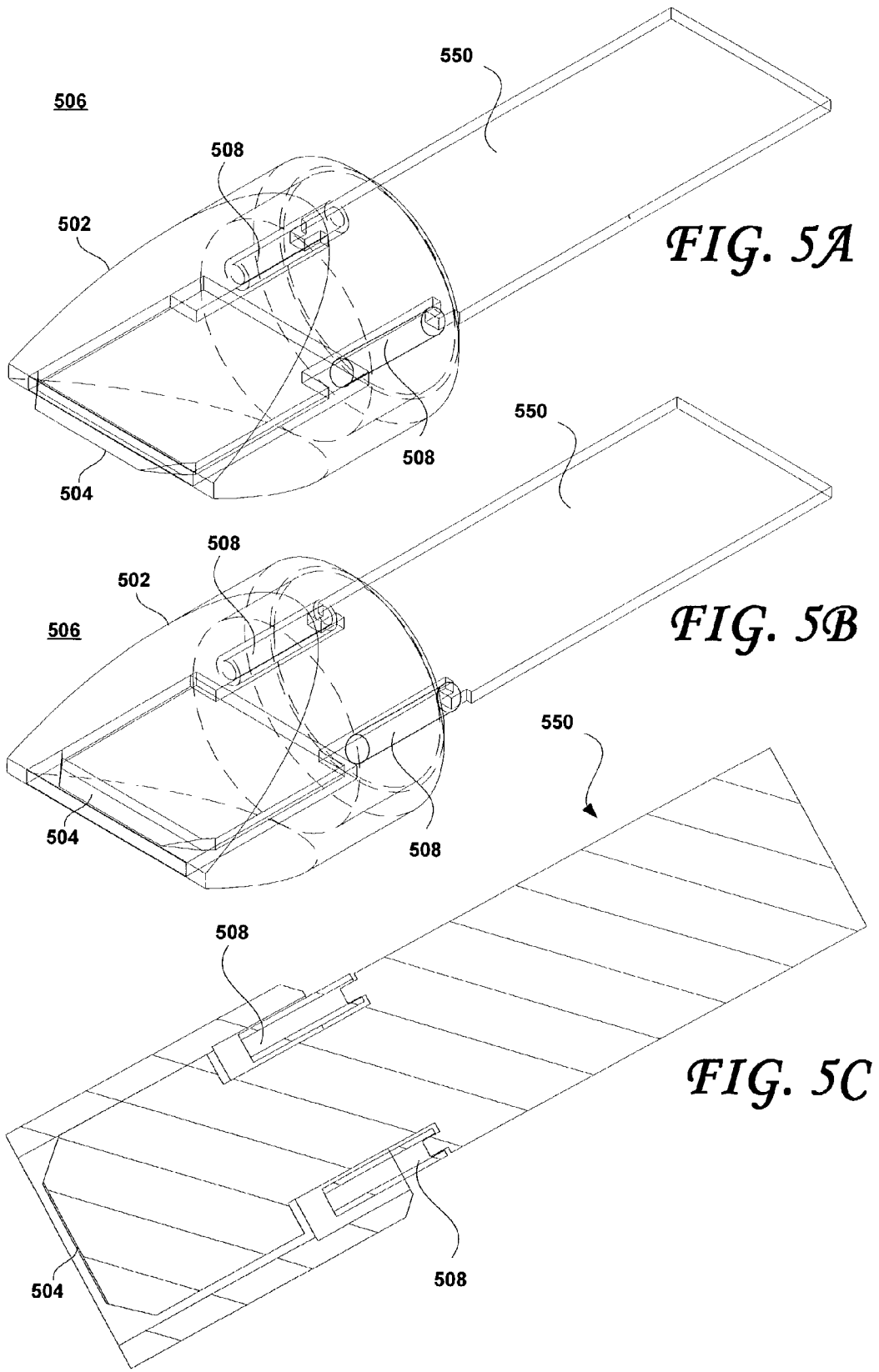
FIG. 5A is a perspective view of a selectively atraumatic and cutting distal tip according to another embodiment of the present invention, in which the cutting surface thereof is in a first configuration that is effective to cut tissue.
FIG. 5B is a perspective view of the cutting tip of FIG. 5A, in which the cutting surface thereof is in a second configuration that is ineffective to cut tissue.
FIG. 5C shows the cutting assembly that includes the cutting surface of the cutting tip of FIGS. 5A and 5B.

FIG. 1A shows an excisional biopsy device having a conventional distal tip. The excisional biopsy device shown in FIGS. 1A through 2B is disclosed in commonly assigned and co-pending US patent application entitled "Methods And Devices For Cutting And Collecting Soft Tissue", Ser. No. 10/189,277 filed on Jul. 3, 2002, the disclosure of which is incorporated herewith by reference in its entirety. As shown, the excisional device 100 includes a proximal section 102 that may be configured to fit the physician's hand (or that may alternatively be configured for a stereotactic apparatus). Extending from the proximal section 102 is a shaft 104 that is terminated by a distal tip 106. The distal tip 106 is configured so as to easily penetrate a mass of tissue. The distal tip 106 may be configured to be energized by a radio frequency (RF) energy source, supplied via the electrical cord 122. However, the distal tip 106 need not be energized, as the cutting surface(s) of the distal tip 106 may be sufficient sharp so as to easily penetrate the tissue to the target excision site. A work element, such as an integrated cut and collect assembly 108 may be mounted near the distal tip 106 or near the distal-most portion of the shaft 104. The integrated cutting and collection assembly 108 is configured to cut a tissue specimen (a piece of tissue or a lesion) from the mass of tissue (such as, for example, breast tissue), to collect the cut specimen and to isolate the cut specimen from the surrounding tissue by, for example, encapsulating and isolating the same within a flexible bag-shaped membrane or sheath 114.

As shown, the integrated cut and collect assembly 108 includes a cutting portion and a collection portion that includes a flexible membrane 114. The collection portion of integrated cut and collect assembly 108 may be attached to the cutting portion. The cutting portion is configured to cut the specimen from the mass of tissue and the collection portion is configured to collect the cut specimen and to isolate the cut specimen from surrounding tissue. This isolation from surrounding tissue may be carried out by a flexible membrane or sheath 114 that forms a part of the collecting portion of the integrated cut and collect assembly 108.

FIG. 2A shows the excisional device of FIGS. 1A and 1B in use, cutting and collecting a specimen of soft tissue and FIG. 2B shows the excisional device of FIG. 2A while being retracted from the patient, illustrating the potential for damage to the sheath 114 of the cut and collect assembly. As shown in FIG. 2A, the excisional biopsy device 100 may be introduced into the patient's soft tissue 908 (such as, for example, breast tissue), positioned adjacent the lesion 904 and the cut and collect assembly extended. This extends the flexible membrane 114 and the cutting portion. The device 100 may then be energized with RF energy and rotated in the direction of arrow 1102. The lesion 904 is then cut and isolated from the surrounding tissue 906 as it is encapsulated within the sheath 114 and isolated from the surrounding tissue 906. As shown in FIG. 2B, after the lesion 904 has been fully cut, separated and isolated from the surrounding tissue 906, the integrated cut and collect assembly may be retracted by manipulation of the actuator 112 (shown in FIG. 1A), which retracts it closer to the shaft 104 to ease the device retraction. The lesion 904 is, as shown in FIG. 2B, encapsulated within the sheath 114, which may at least partially trail the distal tip 106. Because the sheath 114 may trail (or at least come into contact with) the distal tip 106, it may become damaged should the cutting surfaces thereof cut the flexible membrane or sheath 114, which would compromise the isolation of the lesion 904 within the sheath 104. A compromised sheath 114 increases the risks that potentially abnormal cells may be released within the fatty or connective tissue of the breast along the retraction path of the device, for example.

In addition, after the device 100 has been introduced into the patient's tissue 908, the portion of the shaft 104 that is distal to the integrated tissue cutting and collection element (or the portion that is distal to the work element of a similarly constituted surgical instrument) may be considered dead space. That is, after the instrument has been inserted and the work element thereof has been positioned at its operative position within the patient's tissue, the portion of the instrument that is distal to the work element serves no useful purpose and may, in fact, hinder the optimal placement of the instrument within the patient. Indeed, the presence of the distal tip 106 may prevent the surgeon form placing the work element of the surgical instrument (in this case, the integrated cutting and collection assembly 108) in the optimal position, for fear of damaging sensitive structures within the patient. For example, the lesion that is to be removed or biopsied may be located adjacent to ducts 224 or lobules 225 within the female breast or some other organ within the tissue, generically represented at 222. As the surgeon strives to avoid damaging such structures, he or she may not be able to place the device 100 as close to the lesion as necessary, making it difficult to obtain clean margins around the cut lesion. Moreover, the distal tip 106 may, during placement of the device 100 or during retraction thereof, cut through the ductal walls, increasing the potential risk of seeding potentially abnormal cells within the ducts 224 and/or lobules 225.

FIGS. 3A through 15B show a number of alternatives to the distal tip 106 that overcome some or all of the above-outlined problems. Indeed, all of the embodiments illustrated in FIGS. 3A through 15B prevent damage to tissue during retraction of the instrument, and prevent damage to any collection element and any contained collected specimen or lesion during retraction of the device from the patient (or the environment of use). Some of the embodiments presented herewith also advantageously reduce the dead space between the work element of the surgical instrument and the distal-most part thereof and allow the instrument to be positioned very close to sensitive structures. Although the present invention is presented as being includable on an excisional biopsy device such as shown in FIGS. 1A through 2B, it is understood that the present invention is not limited thereto. Indeed, the various embodiments shown in the drawings and described herein below may be fitted onto most any surgical instrument that requires a cutting distal surface to penetrate and create a dissection path through tissue. Any of the embodiments disclosed herein may be energized with RF energy (in which case a sharp cutting surface may not be necessary), but need not be. For example, the embodiments of the present invention may be implemented, with advantageous results on the devices disclosed in U.S. Pat. Nos. 6,387,056 or 6,331,166.

FIGS. 3A and 3B show a first embodiment of a selectively atraumatic and cutting distal tip according to the present invention. As shown, the distal tip 306 shown in FIG. 3A includes a cutting surface or edge 304. The cutting surface 304 may be conical, may be a blade, a wire (which may be RF energized) or any surface configured to cut tissue and create a dissection path for the instrument through the patient's tissue. The distal tip 306 is configured to assume a first configuration in which the cutting is effective to cut tissue (FIG. 3A) and a second configuration in which the cutting surface 304 is ineffective to cut tissue (FIG. 3B). The embodiment of FIGS. 3A and 3B is configured such that advancing the surgical instrument through the tissue causes the tissue to push on the retractable guard 302 and cause it to retract, thereby exposing the cutting surface 304. When the surgical instrument is retracted along the dissection path, the tissue no longer exerts a force (as shown at 310) on the retractable guard 302, and the guard 302 is caused to cover the cutting surface 304. The retractable guard may be biased (by springs such as shown at 308, or some other pneumatic, hydraulic, mechanical or electrical means) to cover the cutting surface unless sufficient force is exerted on the retractable guard 302 to overcome the biasing force. Alternatively, the retractable guard 302 may be configured for manual operation, whereby the surgeon manipulates an actuator to extend and retract the guard 302.

FIGS. 4A and 4B show, in cross-section, another embodiment of the present distal tip 406 that includes a stationary cutting surface and a selectably extendable and retractable guard 402. As shown, the cutting surface 404 extends away from the shaft 104 of the surgical instrument to which the distal tip 406 is mounted. The distal tip 406 is shown in FIG. 4A in a first configuration in which it is effective to cut tissue and in FIG. 4B in a second configuration in which the cutting surface 404 is ineffective to cut tissue. The cutting surface 404 may be a blade, a wire, an edge of a truncated conical solid or any structure that defines a cutting surface, line or points. The cutting surface need not have a sharp edge if the cutting surface thereof is RF energized. However constituted, the cutting surface may be selectively exposed to the tissue (FIG. 4A) and covered so as to no or minimal contact with the surrounding tissue (FIG. 4B). For the distal tip 406 to assume the second configuration in which the cutting surface 402 is ineffective to cut tissue, the retractable guard 402 may be slid in the distal direction (indicated by arrows 410) so as to cover the distal-most tip of the cutting surface. In this embodiment, the retractable guard 402 may be configured as a sleeve over a portion of the shaft 104 that is selectively movable by the surgeon during the intended procedure. The retractable guard may alternatively be disposed adjacent an inner surface of the shaft 104.

FIGS. 5A, 5B and 5C show another embodiment 506 of the present invention, in which a retractable guard covers the cutting surface of the tip. As shown, the retractable guard 502 has a generally truncated conical shape that is well suited to dissect and spread tissue as the surgical instrument (not shown in FIGS. 5A, 5B and 5C) to which this distal tip 506 is attached is advanced through the patient's tissue. FIG. 5A shows the distal tip 506 in a first configuration in which the cutting surface 504 is effective to cut tissue (i.e., is exposed to the tissue), whereas FIG. 5B shows the same distal tip 506 in its second configuration in which the cutting surface 504 thereof is ineffective to cut tissue (i.e., is not exposed to the tissue). As shown in FIG. 5B, the retractable guard 502 is biased to the second configuration in which the cutting surface 504 is covered and ineffective to cut tissue. The biasing force may be applied by springs 508 or any other suitable means. When the surgical instrument to which the selectively atraumatic and cutting distal tip 506 is attached is advanced through tissue, the tissue resists the forward motion of the instrument and overcomes the biasing force of the springs 508 to cause the retractable guard to retract and the cutting surface of the cutter assembly 550 to become exposed to the tissue. As long as the forward motion is maintained and the springs 508 compressed, the cutting surface 504 is exposed to the tissue and cuts therethrough, creating a dissection path as the cut tissue slides on the exposed inclined surfaces of the retractable guard. It is to be noted that in the embodiments of FIGS. 3A and 3B and 5A, 5B and 5C, the springs 508 may be omitted and the guards 302, 502 may be advanced and retracted manually through mechanical, hydraulic, pneumatic or other means. Moreover, in the embodiments of FIGS. 3A and 3B and 5A, 5B and 5C, the cutting surface 304, 504 is stationary and a retractable guard 302, 502 selectively covers and uncovers the cutting surface. Those of skill in this art will recognize other configurations and structures in which a cutting surface is selectively covered and rendered ineffective to cut tissue and uncovered and rendered effective to cut tissue.

Figure 6A:
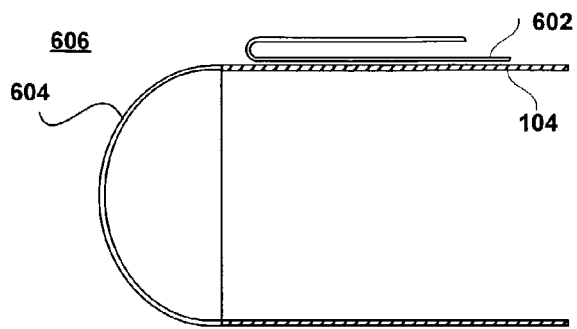
FIG. 6A is a modified cross-section of a selectively atraumatic and cutting distal cutting tip according to another embodiment of the present invention, in which the cutting surface thereof is in a first configuration that is effective to cut tissue.
Figure 6B:
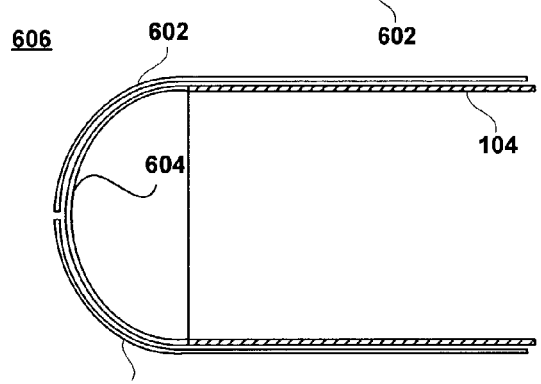
FIG. 6B shows the distal cutting tip of FIG. 6A, wherein the cutting surface thereof is in a second configuration that is ineffective to cut tissue.

Moreover, the retractable guard need not be rigid. As shown in cross-section in FIGS. 6A and 6B, the retractable guard may include a flexible sleeve disposed on the outside (for example) surface of the shaft 104 of the surgical instrument. As shown, such a flexible sleeve 602 may be at least partially folded back on itself as shown in FIG. 6A when the cutting surface 604 of the selectively atraumatic and cutting distal tip 606 is in its first configuration in which the cutting surface 604 is effective to cut tissue. The flexible sleeve 602 may be caused to unfold itself and to at least partially cover the cutting surface 604. The sleeve 602 may be cause to at least partially cover the cutting surface 604 by mechanical means, such as a ring or tube advanced along the surface thereof, by the frictional forces of the tissue acting upon the sleeve 602 during retraction of the device from the patient or by other means. The sleeve 602 may be inflatable. In that case, the sleeve 602 is at least partially deflated in FIG. 6A and at least partially inflated (with $CO_2$, saline or any other safe gas or fluid, for example) when covering the cutting surface 604, as shown in FIG. 6B. Those of skill in this art may device other means of selectively unfolding a sleeve such as shown at 602.

Figure 7A:
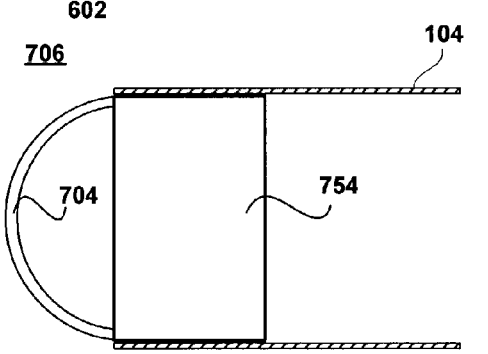
FIG. 7A is a cross-sectional view of a selectively atraumatic and cutting distal tip according to still another embodiment of the present invention, in which the cutting surface thereof is in a first configuration that is effective to cut tissue.
Figure 7C:
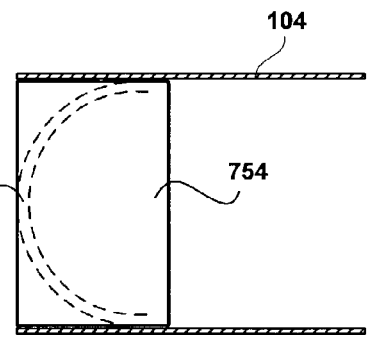
FIG. 7C shows another embodiment of the distal tip of FIG. 7A, in which he cutting surface thereof is in a second configuration that is ineffective to cut tissue.
Figure 7B:
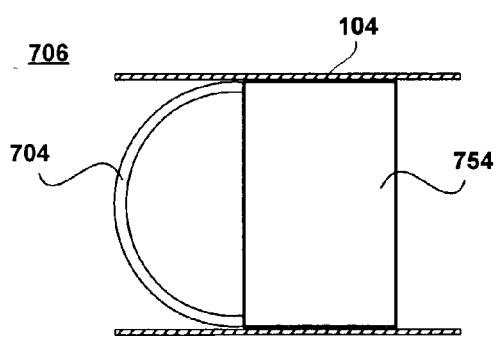
FIG. 7B shows the distal portion of the cutting tip of FIG. 7A, wherein the cutting surface of the distal tip is in a second configuration that is ineffective to cut tissue.

Alternatively, the distal tip may be configured such that the cutting surface is movable. This alternative has the advantage that it decreases the dead space between the work element and the distal-most portion of the shaft, thereby enabling the surgeon to advance the surgical instrument closer to sensitive structures. One such embodiment is shown in cross-sectional FIGS. 7A and 7B. As shown, the cutting surface 704 may be attached to a support 754 that is configured to selectively retract and extend within the shaft 104. The retraction of the support 754 and attached cutting surface 704 may be effectuated by most any means, including mechanical, electrical, electromechanical, hydraulic, pneumatic means, for example. An actuator may be provided on the proximal section of the surgical instrument to control the extension and retraction of the support 754 and attached cutting surface 704. Alternatively, as shown in FIG. 7C, the support 754 may itself be configured to move and/or cover at least a portion of the cutting surface 704.

Figure 8A:
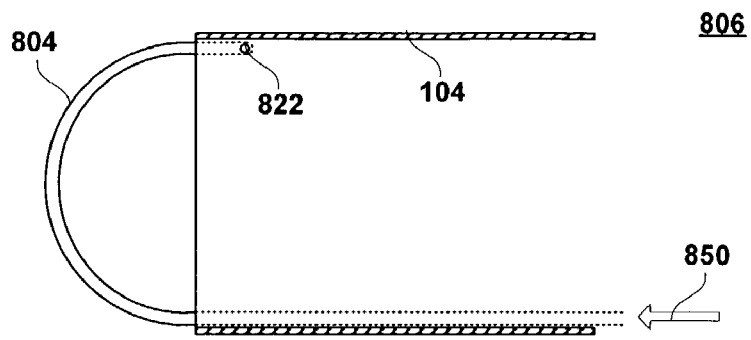
FIG. 8A is a cross-sectional view of a selectively atraumatic and cutting distal tip according to a further embodiment of the present invention, in which the cutting surface thereof is in a first configuration that is effective to cut tissue.
Figure 8B:
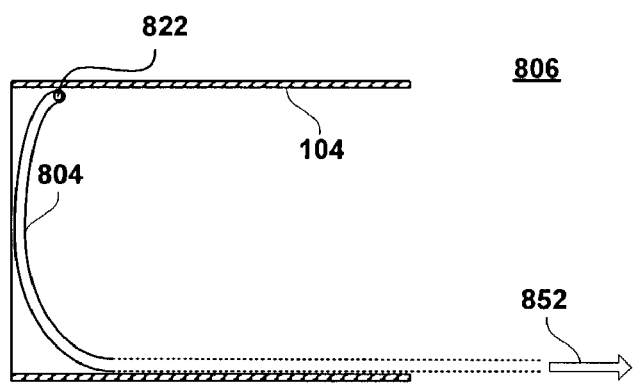
FIG. 8B shows the distal cutting tip of FIG. 8A, wherein the cutting surface thereof is in a second configuration that is ineffective to cut tissue.

Alternatively still, the distal tip may be configured such that the cutting surface (or surfaces) is configured to pivot between the first configuration in which the cutting surface is effective to cut tissue and the second configuration in which the cutting surface is ineffective to cut tissue. Such embodiments also have the advantage of reducing the dead space between the work element and the distal-most portion of the shaft when the cutting surface is in the second configuration. Two examples of such functionality are shown in cross-sectional FIGS. 8A through 9B. Turning first to FIGS. 8A and 8B, there is shown a portion of the shaft 104 to which a pivotable distal tip 806 is fitted. As shown, the cutting surface 804 may include a flexible blade or wire (should the cutting surface be RF energized). For example, the blade may include stainless steel or, for example, a nickel-titanium alloy having shape memory characteristics. According to this embodiment, one end of the cutting surface 804 may be attached to a fixed pivot feature 822 such that the blade bows out when pushed in the direction indicated by arrow 850 in FIG. 8A and retracts within the shaft 104 when the cutting surface 804 is pulled in the direction shown at 852 in FIG. 8B. Alternatively, the cutting surface 804 may be formed of a shape memory material that assumes a first shape (such as that shown in FIG. 8A) at a first temperature (i.e., body temperature) and assumes a second shape (retracted within the shaft 104, as shown in FIG. 8B) at a second temperature (such as room temperature, for example). Alternatively, if the cutting surface 804 is configured to be RF energized, the cutting surface 804 could be configured to assume the shape shown in FIG. 8A at the elevated temperature of an RF energized blade (as it dissipates a portion of the applied energy as heat) and configured to assume the shape shown in FIG. 8B when the RF energy is shut off and the cutting surface cools. Other alternatives may occur to those of skill in this art and all such alternatives are deemed to fall within the scope of this invention. For example, the blade or wire may be mechanically retracted or extended.

Figure 9A:
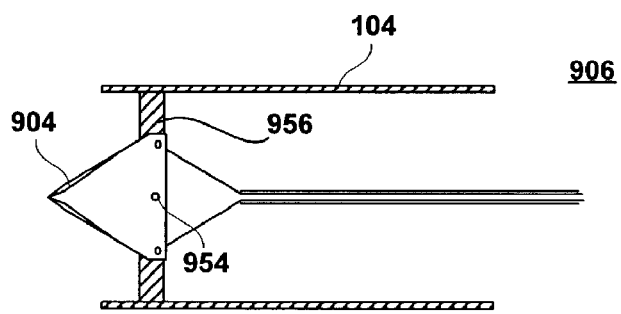
FIG. 9A is a cross-sectional view of a selectively atraumatic and cutting distal tip according to a further embodiment of the present invention, in which the cutting surface thereof is in a first configuration that is effective to cut tissue.
Figure 9B:
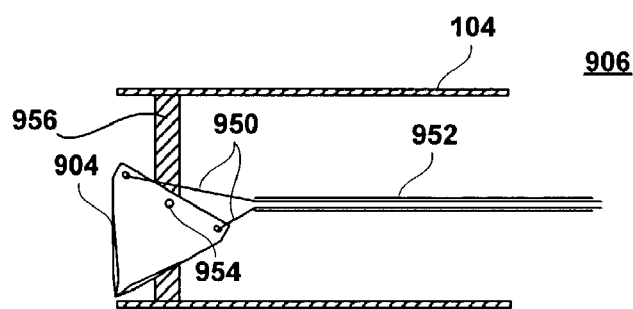
FIG. 9B shows the distal cutting tip of FIG. 9A, in which the cutting surface thereof is in the second configuration that is ineffective to cut tissue.

As shown in cross-sectional FIG. 9A, the cutting surface 904 of the distal tip 906 may be configured to pivot about a central pivot point 954 by means of wires 950 attached thereto. By pulling one wire 950 and loosening another one of the wires 950, the cutting surface 904 may be caused to pivot about its pivot point 954 and to thereby reduce the dead space at the distal end of the surgical instrument to which this distal tip 906 is fitted. The wires 950 may be confined within a passage defined by a tube 952 or within a lumen defined within the shaft 104. Again, the cutting surface 904 may be configured to be RF-energized or may simply include a sharp, non RF-energized edge.

Figure 10A:
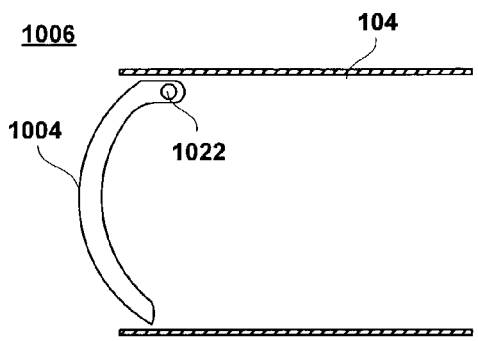
FIG. 10A is a cross-sectional view of a selectively atraumatic and cutting distal tip according to a further embodiment of the present invention, in which the cutting surface thereof is in a first configuration that is effective to cut tissue.
Figure 10B:
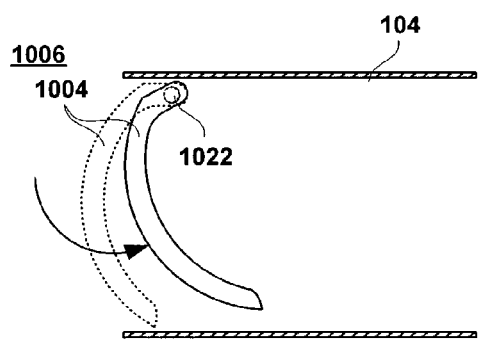
FIG. 10B shows the cutting tip of FIG. 10A, wherein the cutting surface thereof is shown in both the first configuration (dashed lines) that is effective to cut tissue and in the second configuration (solid lines) that is ineffective to cut tissue.

Cross-sectional FIGS. 10A through 12 show various embodiments that include further pivoting cutting surfaces. As shown in FIG. 10A, the cutting surface 1004 of the selectively atraumatic and cutting distal tip 1006 is configured as a curved blade or RF element that pivots about a pivot feature 1022 disposed on the shaft 104. FIG. 10B shows the cutting element 1004 in its first configuration in which it is effective to cut tissue in dotted lines and, in solid lines, the cutting surface 1004 in its second configuration in which it is pivoted about the pivot feature 1022 and in which it is ineffective to cut tissue. This embodiment also has the advantage of reducing the dead space distal of the work element of the surgical instrument to which this distal tip is fitted.

Figure 11A:
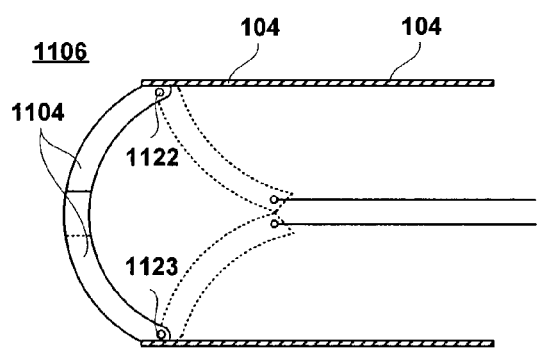
FIG. 11A is a cross-sectional view of a selectively atraumatic and cutting distal tip according to a still further embodiment of the present invention, wherein the cutting surface thereof is shown in both the first configuration (solid lines) that is effective to cut tissue and in the second configuration (dashed lines) that is ineffective to cut tissue.
Figure 11B:
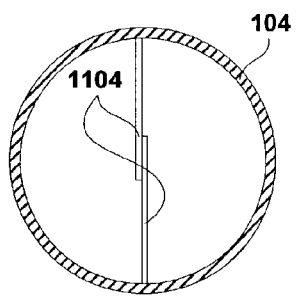
FIG. 11B is a front view of the distal cutting tip of FIG. 11A.

FIGS. 11A and 11B show a side cross sectional view and a front view, respectively, of yet another embodiment 1106 of the present invention. This embodiment includes two cutting surfaces 1104 that pivot about respective pivot features 1122 and 1123 disposed on or near a surface of the shaft 104, for example. The cutting surfaces 1104, as best seen in FIG. 11B, may be offset relative to one another.

Figure 12:
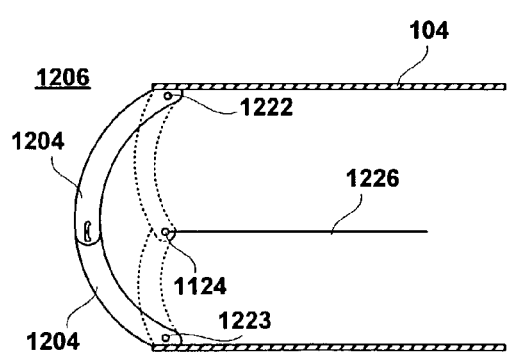
FIG. 12 is a cross-sectional view of a selectively atraumatic and cutting distal tip according to yet another embodiment of the present invention, in which the cutting surface thereof is shown in solid lines in a first configuration that is effective to cut tissue and in dashed lines in a second configuration that is ineffective to cut tissue.
Figure 13:
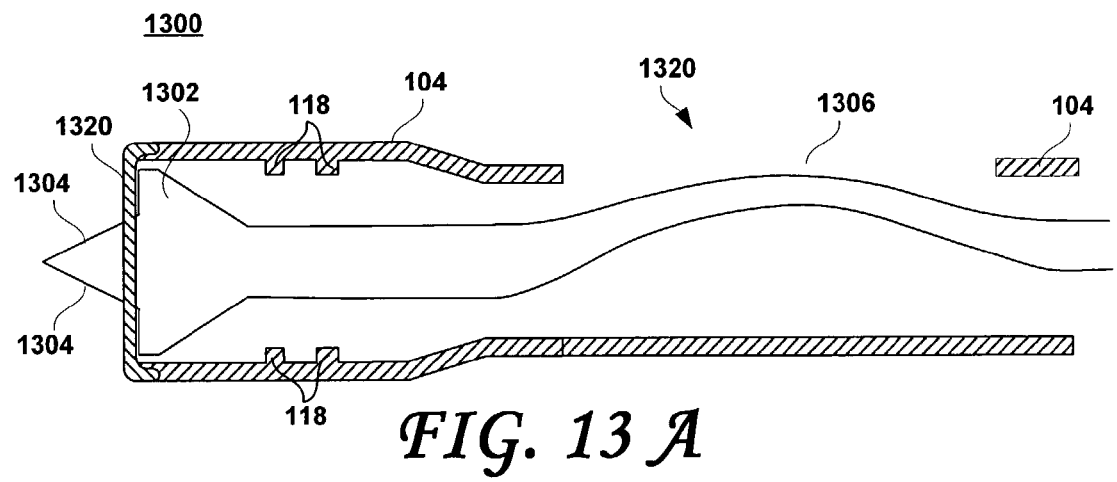
FIG. 13A is a view of a selectively atraumatic and cutting distal tip according to another embodiment of the present invention, in which the cutting surface thereof is in a first configuration that is effective to cut tissue.
FIG. 13B is a perspective view of the cutting tip of FIG. 13A, in which the cutting surface thereof is in a second configuration that is ineffective to cut tissue.
Figure 13:
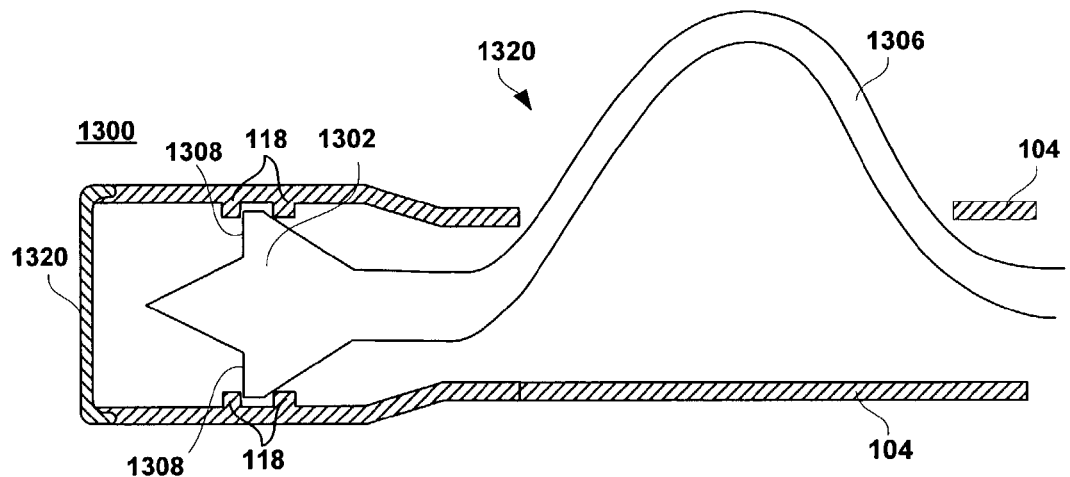

FIG. 12 is a cross-sectional view of still another embodiment. As shown, the selectively atraumatic and cutting distal tip 1206 also includes two cutting surfaces 1204. The cutting surfaces 1204 are coupled together and both pivot about a center pivot 1124 and about pivot points 1222, 1223 disposed on or near the shaft 104 of the surgical instrument. Extension and retraction of the cutting surfaces 1204 may be effectuated using, for example, a wire or rod 1226 or like structure.

FIGS. 13A and 13B illustrate at 1300, in cross-section, an embodiment of the present invention in which the work element of the surgical instrument is integrated with (or at least mechanically coupled to) the selectively atraumatic and cutting distal tip. FIGS. 13A and 13B show the distal portion of an exemplary surgical instrument configured for excisional procedures. As shown, the primary cutter 1306 is configured to be at least partially retracted within a window or fenestration 1320 defined within the shaft 104 (FIG. 13A) and extended out from the window 1320 (FIG. 13B). In use, the cutter 1306 is configured to sever a volume of tissue from the patient as the surgical instrument 1300 is rotated while in the configuration shown in FIG. 13B. A tissue collection device may be coupled to the cutter 1306, as disclosed, for example, in commonly assigned U.S. Pat. No. 6,022,362 and its progeny. The cutter 1306 may be RF energized, but need not be. As shown, a selectively atraumatic and cutting distal tip 1302 may be coupled to the cutter 1306. The distal tip 1302 may be RF energized, but need not be. In the case wherein the cutter 1306 is RF energized and a non-energized tip 1302 is indicated, an insulator may be interposed between the two elements. As shown in FIG. 13A, the cutting surface (or surfaces 1304) of the tip 1302 is in a first configuration wherein it is effective to cut tissue. That is, the cutting surface or surfaces 1304 protrude from the distal-most surface of the instrument 1300. As such, they are configured to cut tissue as the instrument 1300 is inserted into the patient's tissue. A slit may be defined within the distal surface 1320 (which may be or include a flexible elastomeric material, for example). When the instrument has been inserted close to the target location (that is, when the cutter 1306 has been placed adjacent the target location), the surgeon may cause the simultaneous retraction of the cutting surface or surfaces 1304 and the extension of the cutter 1306. As shown, the distal tip 1302 may be retracted until the catch surfaces 1308 of the tip 1302 engage (and optionally lock into) corresponding features 118 in the shaft 104. In this configuration, pushing on the cutter actuator (see reference numeral 112 in FIG. 1A) causes the cutter 1306 (now fixed at its distal end) to extend out of the window 1320 to its operative position. Such a configuration is not limited to a work element such as cutter 1306, but may be adapted to function with most any work element, including for example, reciprocating work elements, rotating work elements and the like. Indeed, the distal tip may be configured to cut through tissue while the primary work element is in an inoperative configuration. The distal tip may transition to a configuration wherein it is ineffective to cut tissue when the primary work element is moved to its operative configuration. The embodiment of the present invention shown in FIGS. 13A and 13B, therefore, is not limited to instruments that includes a cutter that extends radially out of a window defined within the shaft.

Various mechanisms may be used to retract, extend, pivot, cover and uncover the cutting surfaces disclosed herein. For example, a rigid or flexible member coupled to the selectively atraumatic and cutting distal tip may run inside or outside of the surgical instrument to which the tip is fitted. Examples of such rigid or flexible members include tubes, rods, ribbons and wires. Any of these rigid or flexible members may be configured to carry electrical signals or mechanical motion from an actuator (see reference 112 in FIG. 1A) or actuators on the instrument to the cutting surface or surfaces of the present selectively atraumatic and cutting distal tip. Alternatively, a lumen defined within, for example, the shaft 104 may be used to transmit hydraulic or pneumatic signals or force. A syringe, for example, may be used to extend, retract, pivot, cover, uncover, inflate or deflate a portion of the present distal tip.

Figure 14A:
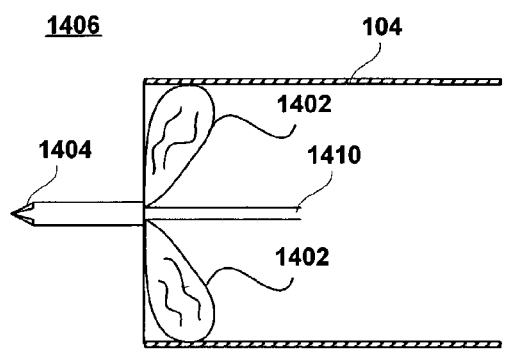
FIG. 14A is a perspective view of selectively atraumatic and cutting distal tip according to another embodiment of the present invention, in which the cutting surface thereof is in a first configuration that is effective to cut tissue.
Figure 14B:
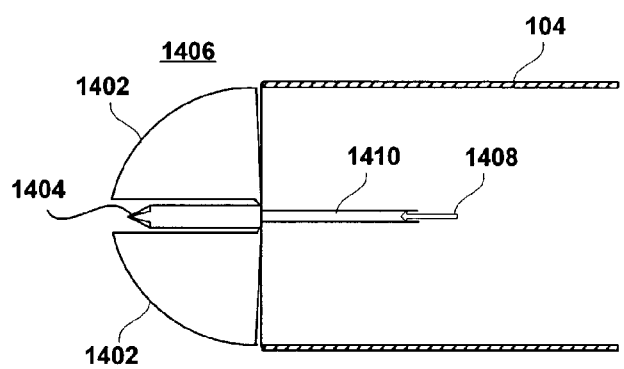
FIG. 14B is a perspective view of the cutting tip of FIG. 14A, in which the cutting surface thereof is in a second configuration that is ineffective to cut tissue.
Figure 15A:
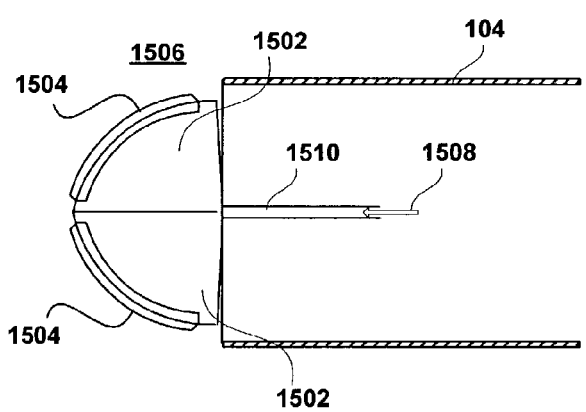
FIG. 15A is a perspective view of a selectively atraumatic and cutting distal tip according to another embodiment of the present invention, in which the cutting surface thereof is in a first configuration that is effective to cut tissue.
Figure 15B:
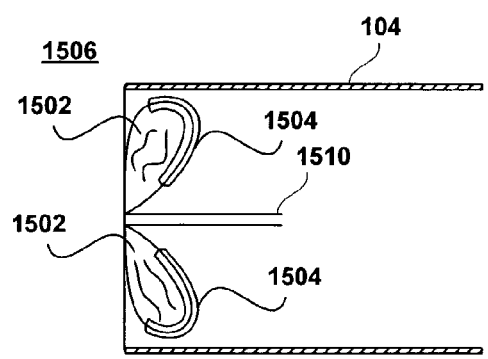
FIG. 15B is a perspective view of the cutting tip of FIG. 15A, in which the cutting surface thereof is in a second configuration that is ineffective to cut tissue.

FIGS. 14A through 15B illustrate other embodiments of the present selectively atraumatic and cutting distal tip. In these embodiments, the cutting surfaces 1404 (FIGS. 14A and 14B) and 1504 (FIGS. 15A and 15B) are selectively covered and uncovered by one or more inflatable bladders 1402 (FIGS. 14A, 14B) or selectively exposed to the tissue by one or more inflatable bladders 1502 (FIGS. 15A, 15B).

Turning first to FIGS. 14A and 14B, the present distal tip 1406 is fitted to the distal end of the shaft 104 and includes one or more cutting surfaces 1404. The shape of the cutting surfaces may be varied according to the application. In FIG. 14A, the distal tip is in a first configuration wherein the cutting surface 1404 is effective to cut tissue as the surgical instrument to which it is attached is advanced through the patient's tissue. The inflatable bladder or bladders 1402, in this configuration, is or are deflated. The inflatable bladder 1402 may advantageously be configured so as to deflate into a space defined within the shaft 104. When the surgical instrument to which this tip 1406 is attached has been correctly placed at the target site within the patient's tissue, the bladder or bladders 1402 may be inflated with a safe gas or fluid 1408 through a supply lumen 1410. The inflated bladder 1402, as shown in FIG. 14B, covers the cutting surface 1404, thereby preventing the cutting surface 1404 from further cutting tissue or the collection device of the surgical instrument during the procedure or during retraction of the instrument from the patient. The surface or surfaces of the inflatable bladder 1402 that contact or may contact the cutting surface 1404 may be reinforced (e.g., may be locally thicker or may be lined with a cut and tear resistant material) as needed.

In FIGS. 15A and 15B, the cutting surface or surfaces 1504 of the selectively atraumatic and cutting distal tip 1506 are disposed on the inflatable bladder 1502. FIG. 15A shows a cross-section of the present distal tip 1506 in a first configuration in which the cutting surface 1504 is effective to cut tissue, whereas FIG. 15B shows the distal tip 1506 in a second configuration in which the cutting surface 1504 is ineffective to cut tissue. When inflated, the bladder 1502 positions the cutting surface or surfaces 1504 attached to the bladder 1502 in the first configuration in which they are effective to cut tissue. When deflated, as shown in FIG. 15B, the cutting surface or surfaces 1504 are positioned in the second configuration in which they are ineffective to cut tissue. The bladder 1502 may be inflated with a safe gas or fluid 1508 (such as $CO_2$ or an aqueous solution such as saline) through a lumen 1510. When the bladder 1502 is deflated, it is collapsed, preferably in a space within the shaft 104. The cutting surface or surfaces 1504 may include a sharp edge so as to efficiently cut through tissue. The cutting surface or surfaces 1504 may also be energized with RF, in which case the cutting surface or surfaces 1504 need not be sharp. If the cutting surfaces 1404 and 1504 (FIGS. 14 and 15) are configured for RF, the inflatable bladders 1402, 1502 are preferably made from a heat resistant material, such as a high temperature elastomer such as silicone, for example. The bladders 1402, 1502 are preferably shaped so as to efficiently spread the tissue cut by the cutting surface or surfaces 1404, 1504.

While the foregoing detailed description has described several embodiments of this invention, it is to be understood that the above description is illustrative only and not limiting of the disclosed invention. A number of modifications will no doubt occur to persons of skill in this art. All such modifications, however, should be deemed to fall within the scope of the present invention. Thus, the invention is to be limited only by the claims as set forth below.

What is claimed is:

1. A method of retrieving a specimen from a mass of tissue, comprising:

providing a device having a proximal and a distal end and including, near the distal end, a tissue cutter adapted to cut the specimen from the mass of tissue and a specimen collector adapted to collect the cut specimen, the device further including a tip disposed at the distal end thereof, the tip being configured to selectably assume a first configuration that is effective to cut tissue and a second configuration that is ineffective to cut tissue, the tip being biased to assume the second configuration;

a first causing step to cause the tip to assume the first configuration;

inserting the device into the mass of tissue with the tip in the first configuration, the inserting step causing the tip to assume the first configuration;

a second causing step to cause the tip to assume the second configuration;

moving the tissue cutter to cut the specimen from the mass of tissue;

moving the tissue collector to collect the cut specimen, and retracting the device from the mass of tissue while the tip remains in the second configuration.

2. The method of claim 1, wherein the method further includes the step of advancing the device within the mass of tissue over a distance substantially equal to a length of the tip after the second causing step.

3. The method of claim 1, wherein the tip is spring-mounted and wherein the second causing step is carried out by stopping a forward movement imposed upon the device in the inserting step.

4. The method of claim 1, wherein the tissue collector moving step draws a thin flexible sheath over the cut specimen.

5. The method of claim 1, wherein the tissue collector moving step includes collecting the specimen and isolating the collected specimen from contact with the surrounding tissue.

6. The method of claim 1, wherein the tip includes a cutting surface that extends away from the distal tip of the device in the first configuration and wherein the second causing step includes at least partially retracting the cutting surface within the tip.

7. The method of claim 1, wherein the tip includes a cutting surface that is exposed to the mass of tissue in the first configuration and not exposed to the mass of tissue in the second configuration.

8. The method of claim 1, wherein the tip includes a cutting surface that is uncovered and exposed to the mass of tissue in the first configuration and wherein the second causing step includes covering the cutting surface such that the cutting surface is not exposed to the mass of tissue.

9. The method of claim 1, wherein the tissue cutter and the tissue collector are integrated and wherein the moving steps are carried out simultaneously.

10. A device to cut and collect a specimen from a mass of tissue, comprising:
a shalt defining a proximal and a distal end;
a cut and collect assembly on the shaft near the distal end, the cut and collect assembly being configured to cut the specimen from the mass of tissue and to collect the cut specimen; and
a selectively atraumatic and cutting tip disposed at the distal end of the shaft, the tip including a tissue cutting surface or edge that is configured to selectably assume a first configuration that is effective to cut tissue and a second configuration that is ineffective to cut tissue, the tip farther including a resilient member that exerts a biasing force that biases the cutting surface or edge to assume the second configuration, the tip being configured such that when the device is advanced into the mass of tissue, a force exerted by the mass of tissue against the tip overcomes the biasing force and causes the tip to assume the first configuration.

11. The device of claim 10, wherein the cutting surface extends beyond the distal end of the shaft when the tip is in the first configuration and wherein the cutting surface is at least partially retracted within the shalt when the tip is in the second configuration.

12. The device of claim 10, wherein the cutting surface extends beyond the distal end of the shaft when the tip is in the first configuration and wherein the cutting surface is at least partially covered when the tip is in the second configuration.

13. The device of claim 10, the tip is configured to pivot between the first and second configurations.

14. The device of claim 10, wherein the tip further includes a selectively inflatable bladder that is configured to cause the cutting surface to assume the first configuration when inflated and the second configuration when deflated.

15. The device of claim 10, wherein the tip further includes a selectively inflatable bladder that is configured to cause the cutting surface to assume the first configuration when deflated and the second configuration when inflated.

16. The device of claim 10, wherein the tissue cutting surface is resiliently deformable and is configured to extend away from the shalt in the first configuration and is configured to retract within the shaft in the second configuration.

17. The device of claim 10, wherein the tip includes a guard that is configured to slide on the shaft to selectively expose and cover the tissue cutting surface.

18. The device of claim 10, wherein the tissue cutting surface is a distal extension of the cut and collect assembly.

19. The device of claim 18, wherein the tissue cutting surface is configured to assume the second configuration when the cut and coiled assembly is operative to cut and collect tissue.

20. A surgical device, comprising:
a shaft defining a proximal and a distal end,
an actuator attached near the proximal end of the shaft
a work element configured to act upon tissue, the work element being coupled to the actuator and disposed near the distal end of the shaft;
a distal tip filled to the distal end of the shaft, the distal tip including an inflatable bladder, the distal tip being configured to assume a first configuration in which the bladder is inflated and the distal lip extends a first distance from the distal end of the shaft and is effective to cut tissue and a second configuration in which the bladder is at least partially deflated and the distal tip extends a second distance from the distal end of the shaft and is ineffective to cut tissue, the second distance being less than the first distance.

21. The surgical instrument of claim 20, wherein the distal tip is coupled to the actuator.

22. The surgical instrument of claim 20, wherein the distal tip is configured to be operated independently of the work element.

23. The surgical instrument of claim 20, wherein the distal tip includes a resiliently deformable cutting surface that is adapted to cut tissue.

24. The surgical instrument of claim 20, wherein the distal tip is coupled to the work element such that when the work element is in an inoperative configuration, the distal tip is in the first configuration and when the work element is in an operative position, the distal tip is in the second configuration.

25. The surgical instrument of claim 20, the distal tip is configured to assume the first configuration when subjected to a temperature that is above a predetermined threshold temperature and to assume the second configuration when subjected to a temperature that is below the predetermined threshold temperature.

26. The surgical instrument of claim 20, wherein the distal tip is biased to assume the second configuration.

27. The surgical instrument of claim 26, wherein the distal tip is coupled to a resilient member that imposes a biasing force on the distal tip, the biasing force causing the distal tip to assume the second configuration until a mechanical force is imposed upon the distal tip that overcomes the biasing force.

28. A method of retrieving a specimen from a mass of tissue, comprising:
providing a device having a proximal and a distal end and including, near the distal end, a tissue cutter adapted to cut the specimen from the mass of tissue and a specimen collector adapted to collect the cut specimen, the device further including a tip disposed at the distal end thereof, the tip including a selectively inflatable bladder that is being configured to selectably assume a first configuration that is effective to cut tissue and a second configuration that is ineffective to cut tissue;

a first causing step to cause the bladder to one of inflate and deflate to cause the tip to assume the first configuration;

inserting the device into the mass of tissue with the tip in the first configuration;

a second causing step to cause the bladder to deflate if the first causing Step caused the bladder to inflate or to deflate if the first causing step caused the bladder to deflate, to cause the tip to assume the second configuration;

moving the tissue cutter to cut the specimen from the mass of tissue;

moving the tissue collector to collect the cut specimen, and retracting the device from the mass of tissue while the tip remains in the second configuration.

29. A device to cut and collect a specimen from a mass of tissue, comprising:
a shalt defining a proximal end a distal end;
a cut and collect assembly on the shaft near the distal end, the cut and collect assembly being configured to cut the specimen from the mass of tissue and to collect the cut specimen; and
a selectively atraumatic and cutting tip disposed at the distal end of the shaft, the tip including a selectively inflatable bladder and a tissue cutting surface or edge, the cutting surface or edge being configured to selectably assume:
a first configuration that is effective to cut tissue when the bladder is inflated and a second configuration that is ineffective to cut tissue when the bladder is deflated, or
a first configuration that is effective to cut tissue when the bladder is deflated and a second configuration that is ineffective to cut tissue when the bladder is inflated.

30. A device to cut and collect a specimen from a mass of tissue, comprising:
a shaft defining a proximal and a distal end;
a cut and collect assembly on the shaft near the distal end, the cut and collect assembly being configured to cut the specimen from the mass of tissue and to collect the cut specimen; and a selectively atraumatic and cutting tip disposed at the distal end of the shaft, the tip including a tissue cutting surface or edge that is configured to selectably assume a first configuration that is effective to cut tissue and a second configuration that is ineffective to cut tissue, the tip further including a guard that is configured to slide on the shaft to selectively expose and cover the tissue cutting surface.

31. A surgical device for acting upon biological tissue, comprising:
a shaft defining a proximal end and a distal end;
a work assembly adapted to act upon the tissue, the work assembly being disposed near the distal end of the shaft and including a sheath that is configured to at least partially trail the distal end of the shaft as the device is removed from the tissue, and
a distal tip, the distal tip including a cutting surface that is adapted to cut the tissue, the distal tip including a selectively inflatable bladder that is configured to selectively uncover the cutting surface when the device is inserted into the tissue and to cover the cutting surface as the device is removed from the tissue so the cutting surface does not damage the sheath.

32. The surgical device of claim 31, wherein the cutting surface is adapted to be energized by an RF energy source.

33. The surgical device of claim 31, wherein the cutting surface is effective to dissect the tissue when the device is inserted into the tissue.

34. The surgical device of claim 31, wherein the sheath includes a thin flexible membrane.

35. The surgical device of claim 31, wherein the work assembly includes a tissue cutter and wherein the sheath is configured to collect the tissue cut by the tissue cutter.

36. The surgical device of claim 35, wherein the sheath is attached to the tissue cutter.

37. The surgical device of claim 35, wherein the sheath is configured to isolate the cut tissue from surrounding tissue.

38. The surgical device of claim 31, wherein the cutting surface is formed of a shape memory material.

39. The surgical device of claim 31, wherein the cutting surface is coupled to the work element such that when the work element is in an inoperative configuration, the cutting surface is effective to cut tissue and when the work element is in en operative position, the cutting surface is ineffective to cut tissue.

40. The surgical device of claim 31, wherein the cutting surface is configured to pivot between a first configuration in which it is effective to cut tissue and a second Configuration in which is ineffective, to cut tissue.

41. A surgical device for acting upon biological tissue, comprising:
a shaft defining a proximal end and a distal end;
a work assembly adapted to act upon the tissue, the work assembly being disposed near the distal end of the shaft and including a sheath that is configured to at least partially trail the distal end of the shall as the device is removed from the tissue, and
a distal tip, the distal tip including selectively inflatable bladder and a cutting surface that is adapted to cut the tissue, the bladder being configured to expose the cutting surface to surrounding tissue when inflated and to move the cutting surface away from the surrounding tissue when deflated so the cutting surface does not damage the sheath as the device is removed from the tissue.

42. The surgical device of claim 41, wherein the cutting surface is adapted to be energized by an RF energy source.

43. The surgical device of claim 41, wherein the cutting surface is effective to dissect the tissue when the device is inserted into the tissue.

44. The surgical device of claim 41, wherein the sheath includes a thin flexible membrane.

45. The surgical device of claim 41, wherein the work assembly includes a tissue cutter and wherein the sheath is configured to collect the tissue cut by the tissue cutter.

46. The surgical device of claim 45, wherein the sheath is attached to the tissue cutter.

47. The surgical device of claim 45, wherein the sheath is configured to isolate the cut tissue from surrounding tissue.

48. The surgical device of claim 41, wherein the cutting surface is formed of a shape memory material.

49. The surgical device of claim 41, wherein the cutting surface is coupled to the work element such that when the work element is in an inoperative configuration, the cutting surface is effective to cut tissue and when the work clement is in an operative position, the cutting surface is ineffective to cut tissue.

50. The surgical device of claim 41, wherein the cutting surface is configured to pivot between a first configuration in which it is effective to cut tissue end a second configuration in which is ineffective to cut tissue.

* * * * *

UNITED STATES PATENT AND TRADEMARK OFFICE
CERTIFICATE OF CORRECTION

PATENT NO. : 7,029,451 B2
APPLICATION NO. : 10/290051
DATED : April 18, 2006
INVENTOR(S) : Scott C. Anderson et al.

It is certified that error appears in the above-identified patent and that said Letters Patent is hereby corrected as shown below:

Column 17, line 35, replace [shalt] with -- shaft --.

Column 17, line 45, replace [farther] with -- further --.

Column 18, line 14, replace [colled] with --collect--.

Column 18, line 18, after "shaft", inser -- ; --.

Column 18, line 22, replace [filled] with -- fitted --.

Column 18, line 68, delete [being].

Column 19, line 9, replace [Step] with -- step --.

Column 19, line 21, replace [shalt] with -- shaft --.

Column 19, line 21, replace [end] with -- and --.

Column 20, line 19, replace [en] with -- an --.

Column 20, line 23, replace [Configuration] with -- configuration --.

Column 20, line 24, after "which" insert -- it --.

Column 20, line 24, replace [ineffective,] with -- ineffective --.

Column 20, line 31, replace [shall] with -- shaft --.

UNITED STATES PATENT AND TRADEMARK OFFICE
CERTIFICATE OF CORRECTION

PATENT NO. : 7,029,451 B2
APPLICATION NO. : 10/290051
DATED : April 18, 2006
INVENTOR(S) : Scott C. Anderson It is certified that error appears in the above-identified patent and that said Letters Patent is hereby corrected as shown below:

Column 20, line 66, after "which", insert -- it --.

Signed and Sealed this

First Day of August, 2006

JON W. DUDAS
*Director of the United States Patent and Trademark Office*